United States Patent
Salinger et al.

(10) Patent No.: US 9,974,633 B2
(45) Date of Patent: May 22, 2018

(54) DENTAL IMPLANT WITH A PROTECTIVE FILM

(71) Applicants: Stephen Salinger, Deerfield, IL (US); Leslie B Heffez, Deerfield, IL (US)

(72) Inventors: Stephen Salinger, Deerfield, IL (US); Leslie B Heffez, Deerfield, IL (US)

(*) Notice: Subject to any disclaimer, the term of this patent is extended or adjusted under 35 U.S.C. 154(b) by 0 days. days.

(21) Appl. No.: 15/344,126

(22) Filed: Nov. 4, 2016

(65) Prior Publication Data

US 2017/0128175 A1    May 11, 2017

Related U.S. Application Data

(60) Provisional application No. 62/252,322, filed on Nov. 6, 2015.

(51) Int. Cl.
| | |
|---|---|
| *A61C 13/02* | (2006.01) |
| *A61C 13/07* | (2006.01) |
| *A61C 8/00* | (2006.01) |
| *A61C 13/15* | (2006.01) |
| *A61K 6/00* | (2006.01) |
| *A61K 6/06* | (2006.01) |
| *A61K 6/08* | (2006.01) |

(52) U.S. Cl.
CPC ........ *A61C 13/0025* (2013.01); *A61C 8/0074* (2013.01); *A61C 19/003* (2013.01); *A61K 6/002* (2013.01); *A61K 6/06* (2013.01); *A61K 6/08* (2013.01)

(58) Field of Classification Search
CPC ...................................................... A61C 13/25
USPC ........................................................ 433/168.1
See application file for complete search history.

(56) References Cited

U.S. PATENT DOCUMENTS

| | | | | | |
|---|---|---|---|---|---|
| 3,151,393 | A * | 10/1964 | Holmes | ................ | A61C 9/0033 433/218 |
| 3,541,689 | A * | 11/1970 | Snead | ................ | A61C 9/0033 433/141 |
| 5,499,918 | A * | 3/1996 | Morgan | ................ | A61C 8/0069 433/173 |
| 6,155,831 | A * | 12/2000 | McGuire | ............... | A61C 8/0006 433/138 |
| 6,244,868 | B1 * | 6/2001 | Schappert | ............ | A61C 8/0006 433/173 |
| 2006/0046229 | A1 * | 3/2006 | Teich | ................... | A61C 8/0022 433/173 |
| 2007/0196785 | A1 * | 8/2007 | Matheson | ............ | A61C 9/0033 433/136 |
| 2009/0123891 | A1 * | 5/2009 | Rosenberg | ............. | A61C 8/005 433/174 |
| 2010/0151423 | A1 * | 6/2010 | Ranck | ................ | A61C 13/0001 433/193 |
| 2012/0183921 | A1 * | 7/2012 | Karlsson | ................... | A61O 5/20 433/49 |
| 2013/0101964 | A1 * | 4/2013 | Fudim | .................. | A61C 8/0001 433/214 |
| 2013/0288202 | A1 * | 10/2013 | Hochman | ............. | A61C 8/008 433/175 |
| 2013/0330690 | A1 * | 12/2013 | Svensson | ................. | A61O 5/10 433/219 |

(Continued)

*Primary Examiner* — Cris L Rodriguez
*Assistant Examiner* — Matthew Saunders (57) ABSTRACT

The present invention relates to oral care and dental implants. In particular, the present invention is a dental implant with a removable protective film that is used to prevent implant loss and remove unwanted residual cement.

21 Claims, 8 Drawing Sheets

(56) References Cited

U.S. PATENT DOCUMENTS

2016/0022378 A1* 1/2016 Hansen .............. A61C 13/0001
433/219

* cited by examiner

DENTAL IMPLANT WITH A PROTECTIVE FILM

CLAIM OF PRIORITY

This application claims the benefit of priority U.S. Provisional Application No. 62/252,322, entitled DENTAL IMPLANT WITH A PROTECTIVE FILM, filed on Nov. 6, 2015, which is herein incorporated by reference in its entirety.

FIELD OF THE INVENTION

The present invention relates to oral care and dental implants. In particular, the present invention is a dental implant with a removable protective film that is used to prevent implant loss and remove unwanted residual cement.

BACKGROUND OF THE INVENTION

Natural teeth may be lost due to dental disease or trauma. Dental implants are used as replacements for missing teeth and generally comprise three primary components: Fixture, Abutment, and Crown. The fixture are implanted into the bone and is coupled to the abutment which extends outside of the gingiva. The abutment is screwed into the fixture and the crown is cemented on to the abutment, providing a chewing surface that may be analogous to a tooth.

Dental implants are a very predictable method to replace missing teeth, but they can fail. In the case of failure, they will need to be removed for a variety of reasons that may include but are not limited to, the fracture of either the screw or the abutment or bone loss caused by infection or inflammation. A primary cause of implant failure has been linked to retained cement on the base of the abutment that the dentist was unable to remove or unaware of after cementing the crown. Any cement left on the abutment after cementing the crown may cause inflammation of the periodontal tissues and ultimately lead to bone loss and loss of the implant itself. It does not matter the type of cement used, any variety can trigger this inflammatory process. Currently, the removal of the cement is left to the skill of the practitioner. Unfortunately, due to tissue morphology, sub gingival level or simply the shape of the abutment may make it impossible for even the most talented operator to completely remove all of the cement.

It is therefore an objective of the present invention to introduce a dental implant abutment with a protective film, which will help prevent implant loss due to residual cement, by giving the practitioner an easy and effective means to remove cement after cementing the crown in place. The film may be used with all abutment designs used in the current market. The film itself is made of Teflon, Teflon type plastic film coating, adhesive plastic tape or similar materials that is placed on the abutment, completely covering the exposed area of the abutment between the implant itself and the margin of film, which is similar to the plastic covers on many new electrical devices may be placed on the abutment by the manufacturer prior to adjusting or prepping the abutment for the crown or by the dental lab or dentist. The film may be held in place by with an appropriate adhesive on the inside of the film or could be retained via electrostatic means. The film is easily removed leaving no residue by pulling the free end which either extends out from below the tissue or overlaps the other end with the fingers, cotton forceps, hemostat, or a similar instrument. When the film is pulled off, it takes with it any cement which may have flowed out when the crown was sealed and cemented. The film may be modified or extended outward to a variable degree for example, to a shape in which it has an annular J-type ridge or bead at the apical to catch and prevent excess cement from extending past the junction of the abutment and the implant body or at the coronal edge to prevent excess cement from extending past the junction of the crown and the abutment.

The film, which may be colored or clear, cannot break easily and is thin enough as not to displace or hurt the tissue when seating the abutment or removing the film. The free end must extend sufficiently from the soft tissue and be of adequate length to be able to be grasped for removal. It must also be of sufficient strength not to break or tear upon removal. The film may or may not be radiopaque to assure that there is not tape/film remaining on the abutment post removal. It must also be of sufficient strength and adherence that it will not come off during preparation by the lab or the dentist and that it will not shift or come off during seating of the abutment and cementation of the crown.

DETAIL DESCRIPTIONS OF THE INVENTION

All illustrations of the drawings are for the purpose of describing selected versions of the present invention and are not intended to limit the scope of the present invention.

In view of the aforementioned problem(s), the present invention is a dental abutment for an implant with a protective film that can be used with any type or manufacturer of implants, which will help prevent implant loss caused by residual cement, by giving the practitioner an easy and effective means to remove cement after cementing the crown in place. Before explaining at least one embodiment of the present invention in detail, it is to be understood that the device is not limited in its application to the details of the components and arrangements as described or illustrated. The invention is capable of other embodiments and of being utilized and carried out in various ways. It is also to be understood that the phrasing and terminology employed herein are for the purpose of description and should not be regarded as limiting. As such, the present invention is primarily used for oral care, but the device may be applied to many other settings, situations, and scenarios.

Figure 1:
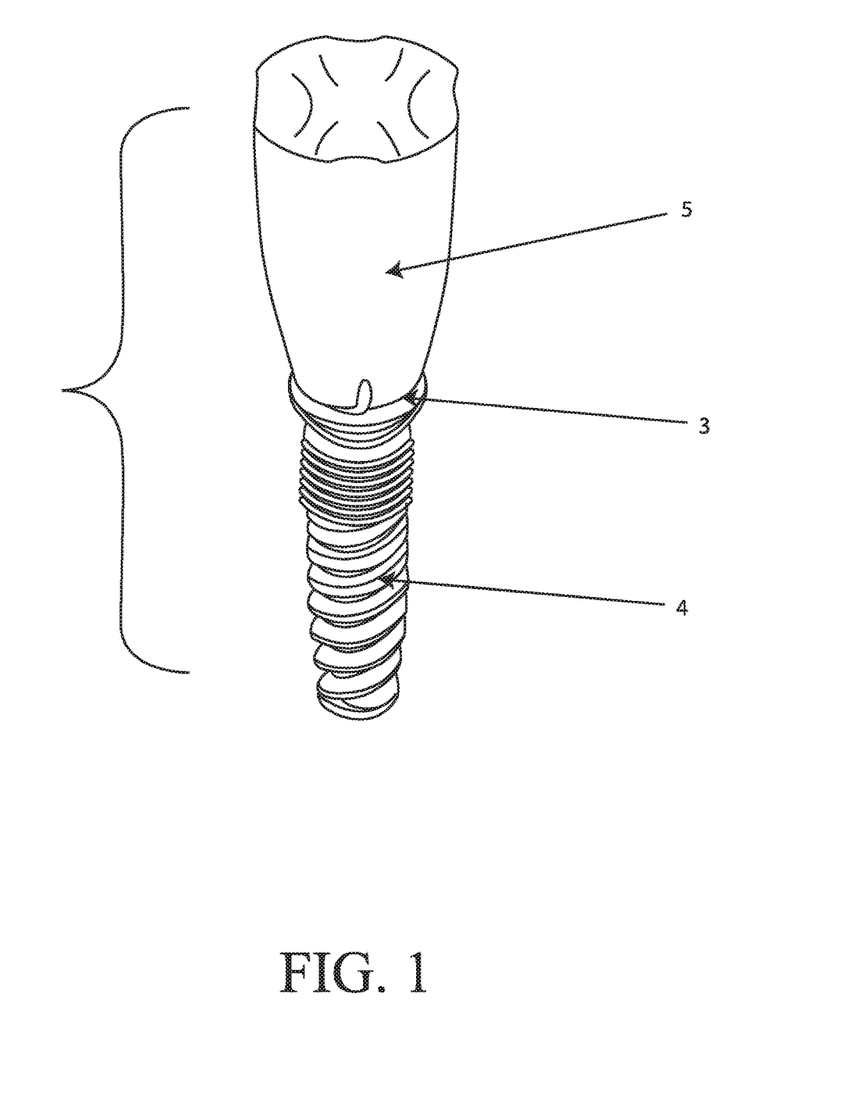
FIG. 1 is a perspective view of the fully assembled present invention, with the film bent to form a J-shaped ridge.
Figure 2:
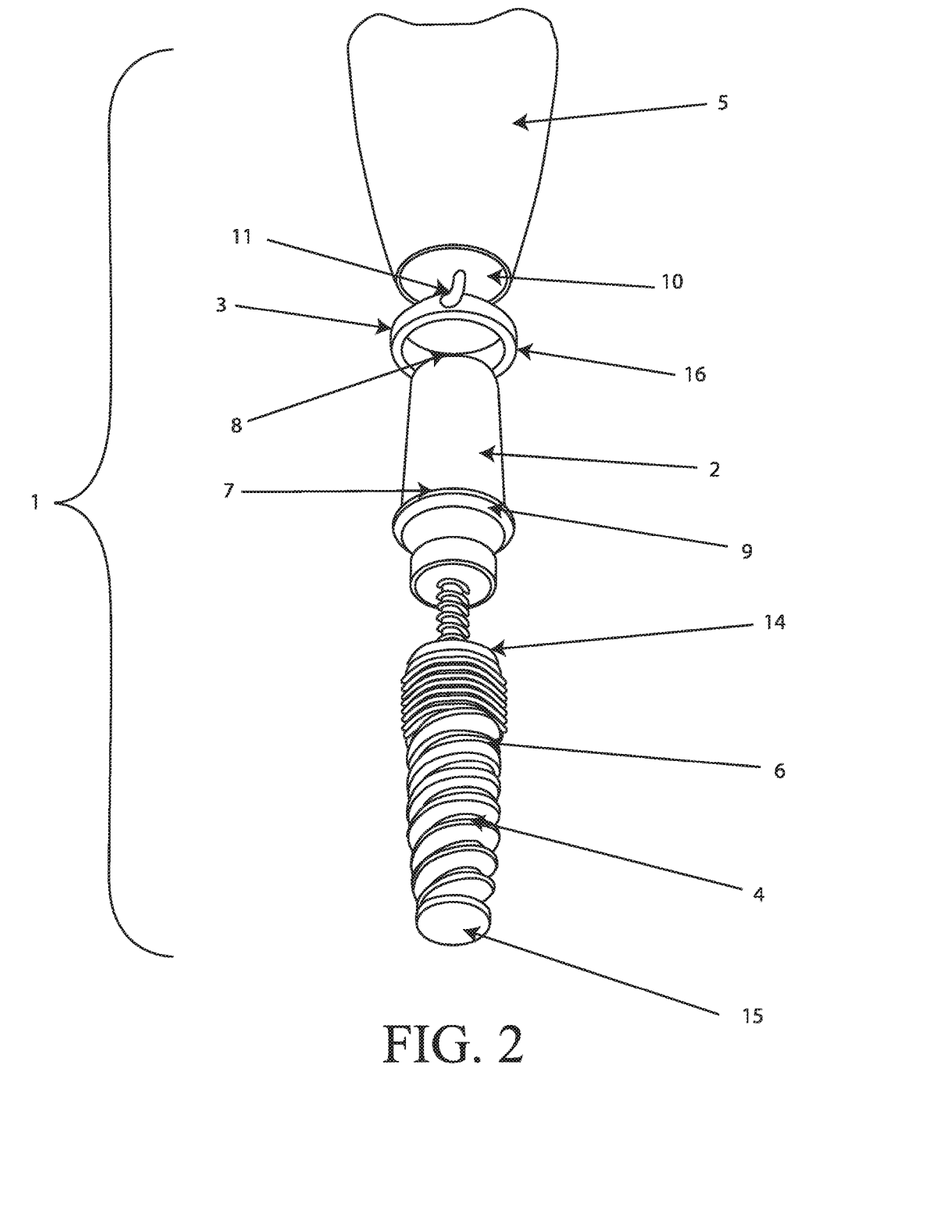
FIG. 2 is an exploded perspective view of the present invention.
Figure 3:
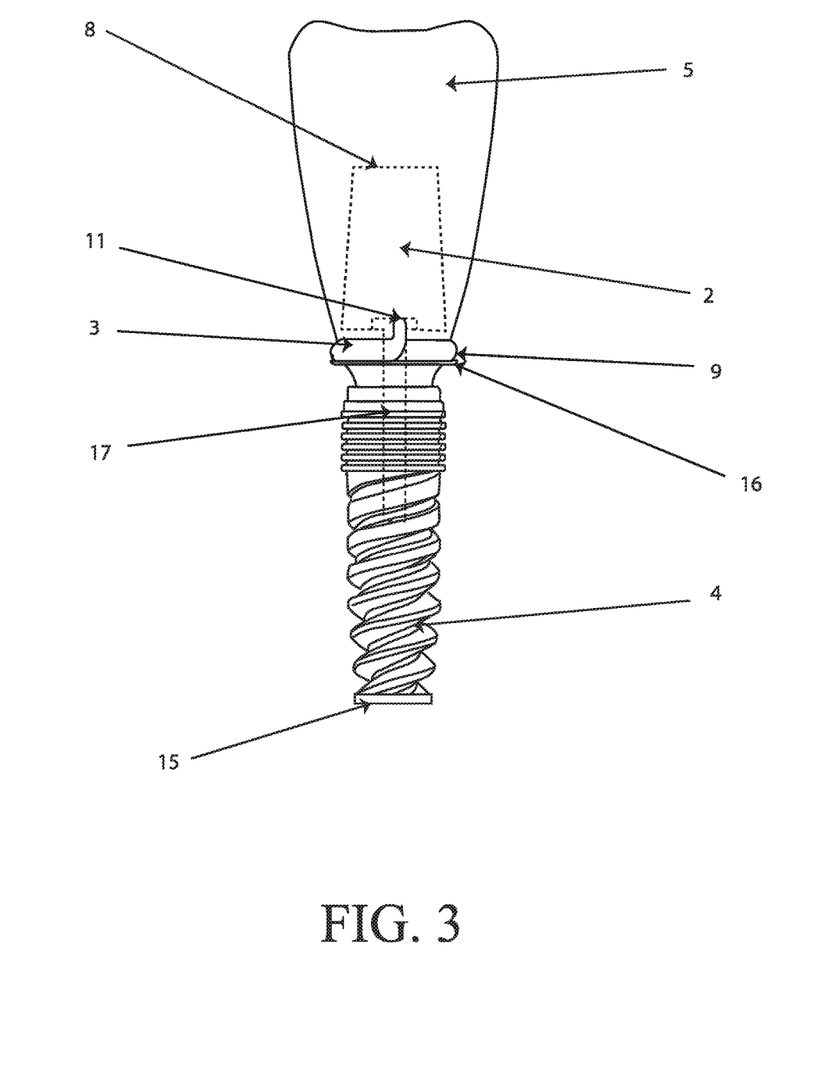
FIG. 3 is an elevated front-side view of the present invention, with a broken line representing the abutment's non-threaded end which fits under the crown, as well as a small portion of the film on that portion of the abutment that does not fit under the crown cavity, and a screw.
Figure 4:
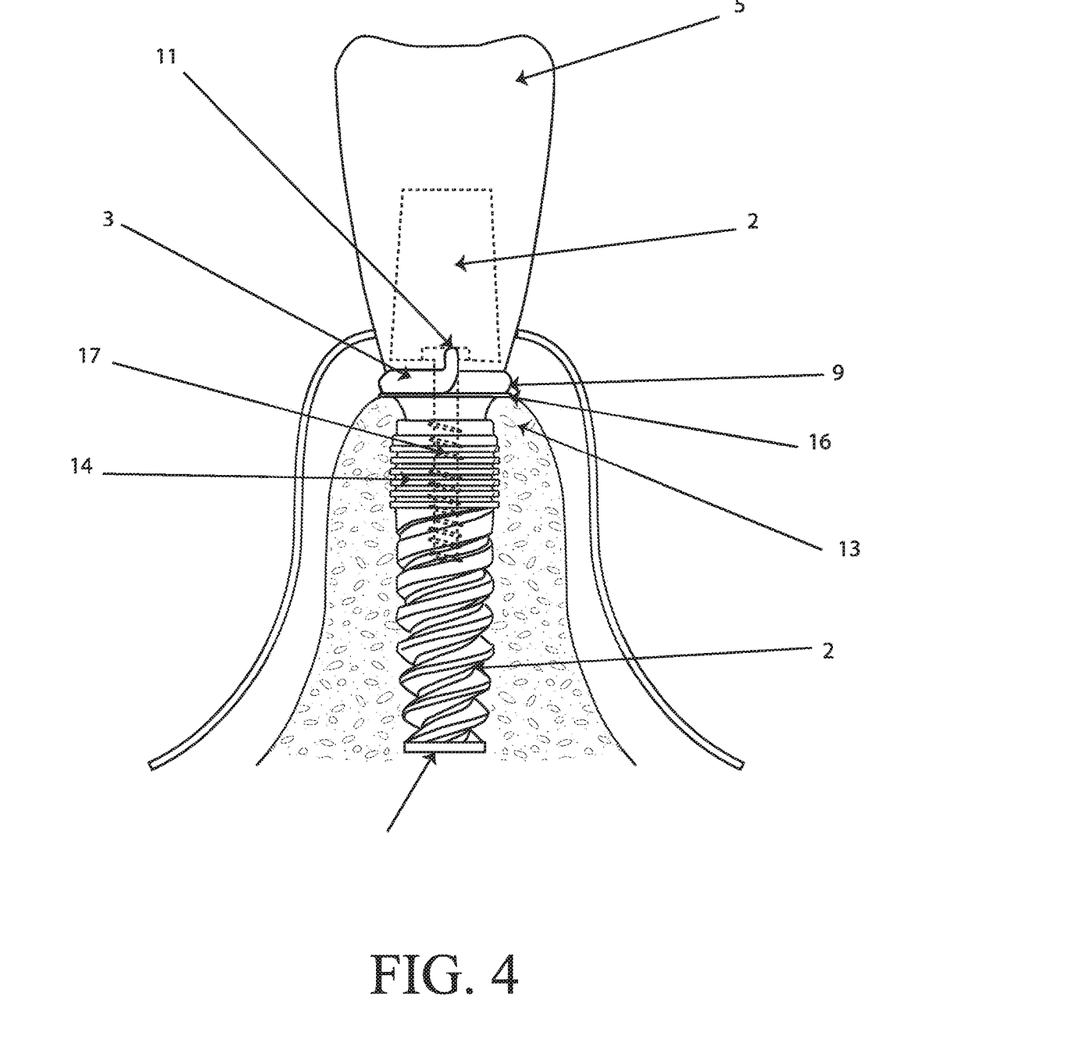
FIG. 4 is a view of the present invention implanted into a patient's mouth, with the fixture screwed into bone.
Figure 5:
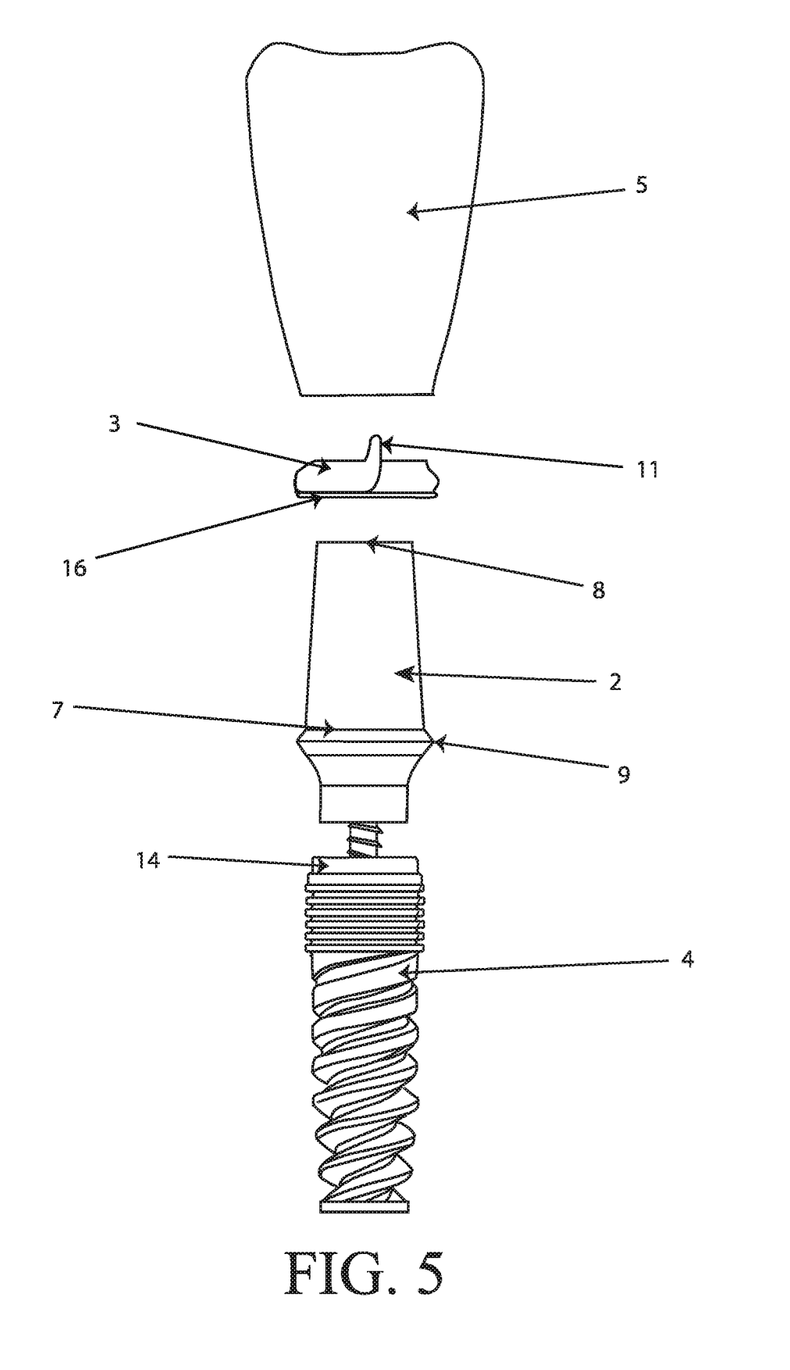
FIG. 5 is an exploded front-side view of the present invention.
Figure 6:
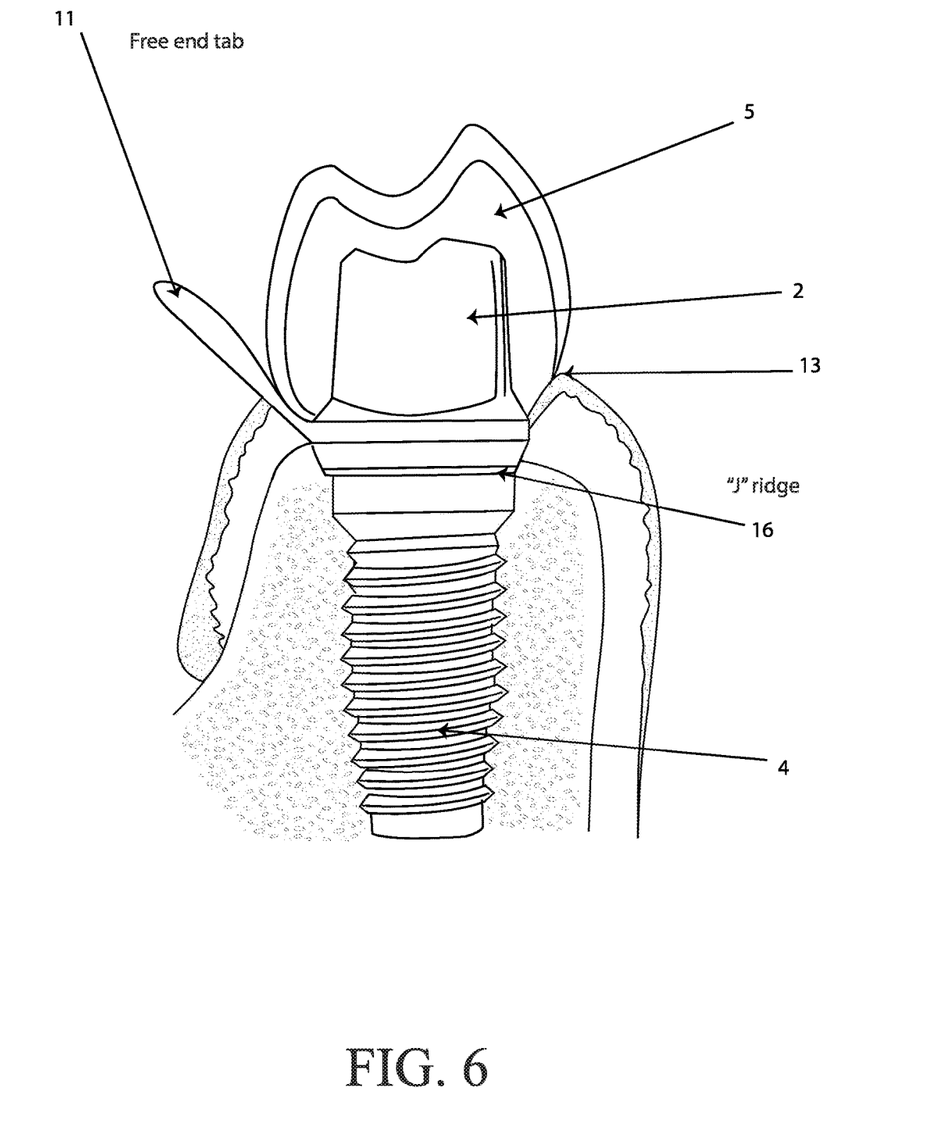
FIG. 6 displays the present invention implanted into a patient's mouth, with the fixture screwed into the bone and J-shaped ridge located around an edge of the film.
Figure 7:
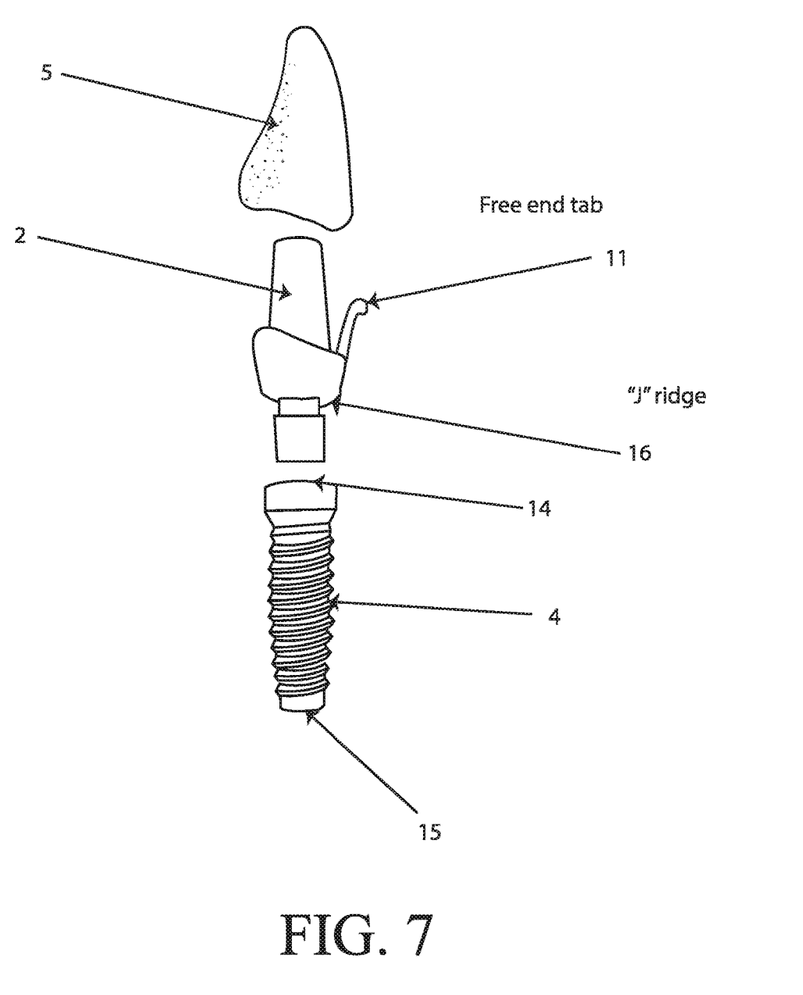
FIG. 7 is a sketch of the present invention in an exploded stated. In this sketch, the J-shaped ridge is visible around an edge of the film.
Figure 8:
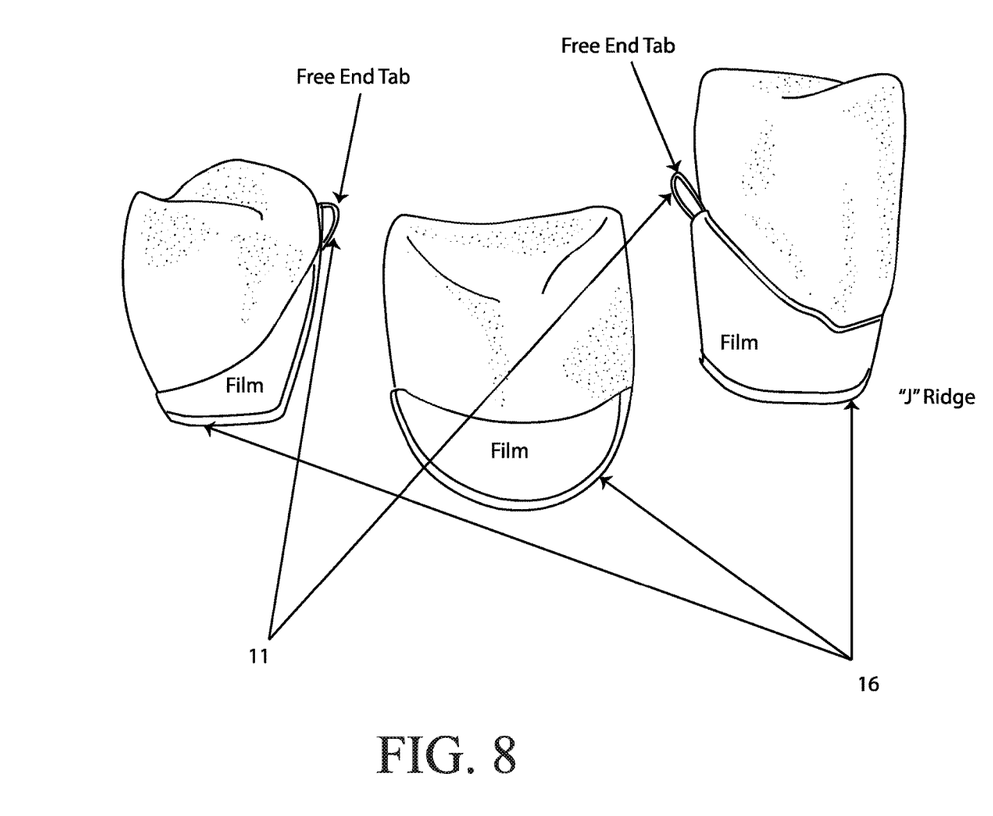
FIG. 8 displays multiple perspective views of the fully assembled present invention. One perspective view displays the J-shaped ridge at the film's coronal edge, while another view displays the J-shaped ridge at the film's apical edge.

As shown in FIGS. 1-8, in the preferred embodiment, the present invention is a dental implant device, the dental implant device comprises an abutment 2, a protective film 3, a fixture 4 and a crown 5. The fixture 4 further comprises a shaft 6 and a threaded cavity 14. The abutment 2 comprises an apical end 7, a non-apical end 8 over which the crown 5 is affixed and an annular protuberance 9. The crown 5 further comprises a crown cavity 10. The protective film 3 further comprises a free end 11 and a non-free end 12. The protective film 3 is selected from the group consisting of polytetrafluroethylene, cellulose film, polyvinyl chloride, polyvinylurethane, silicone and other natural and artificial polymers.

As shown in FIG. 1-8, in the preferred embodiment of the present invention, the fixture 4 is a rigid elongated shaft 6 with two ends opposite from each other. One end of the fixture is closed 15 and is inserted/screwed into the bone of a patient below the gingiva 13. The threaded cavity 14 is located at the other end of the fixture 4, going into the shaft 6 a short distance towards the closed end 15. The threaded cavity 14 is shaped and dimensioned to engage with and receive the abutment's apical end 7, allowing the abutment 2 to be screwed into the fixture 4. The crown cavity 10 is shaped and dimensioned to receive the entirety of the prepared portion of the abutment 2.

As shown in FIG. 1-8, in the preferred embodiment of the present invention, the fixture 4 comprises a shaft 6 and a threaded cavity 14, and the abutment 2 comprises an apical end 7 and a non-apical end 8 onto which the crown 5 is affixed and an annular protuberance 9 between said abutment and said crown. The annular protuberance 9 is the widest portion of the abutment 2 and sits parallel to and in between the apical end 7 which is inserted into the fixture 4 and the non-apical end 8 which receives the crown 5, the annular protuberance's surface being positioned either sub-gingival or supra-gingival.

As shown in FIG. 1-8, in the preferred embodiment of the present invention, the abutment 2 is a rigid member with an apical end 7 that is coupled with the fixture 4 via a screw 17 or force fit that sits opposite the non-apical end 8. The crown 5, which becomes the chewing surface and is analogous to a tooth in function, is cemented onto the abutment's non-apical end 8, which engages with and is received by the crown cavity 10. For means of securement, a cement may be placed in the crown cavity 10, on and by the abutment's non-apical end 8 or both. The cement is selected from the group consisting of zinc phosphate, glass ionomer, resin modified ionomer and a resin cement. The resin cement is selected from the group consisting of a light cured cement, a dual cured cement and an auto-cured cement, the dual-cured cement is used when light penetration is likely to be poor, the dual-cured cement and the auto-cured cement each further comprises a bonding agent where light exposure in dental preparation is difficult. The annular protuberance 9 is the widest portion of the abutment 2, which sits parallel to and in between the apical end 7 which inserts into the fixture 4 and non-apical end 8 which receives the crown 5. The annular protuberance's 9 surface sits either sub-gingival or supra-gingival. The cavity of the crown 10 is shaped and dimensioned to receive the entirety of the prepared portion of the abutment 2. The film 3 will cover the entirety of the annular protuberance's surface 9, with its free end 11 overlapping on top of the non-free end 12. As such, the film 3 will cover the exposed area of the annular protuberance 9 between the fixture 4 and the margin of the crown 5 when the implant 1 is properly placed, with all its components properly connected. Additionally, the film 3 will extend outwards up to the soft tissue/gingiva 13. The film 3 will be made of Teflon, Teflon type plastic film coating, or similar material often found covering new electrical devices.

As shown in FIG. 1-8, in the preferred embodiment of the present invention, the film 3 may or may not have an adhesive on one or both of its sides, preventing it from coming off of the abutment 2 or shifting in unwanted circumstances. The film 3 itself will be of sufficient strength not to tear or break and it will not easily come off the abutment 2 or shift in unwanted circumstances, however, it will be easy enough to remove by pulling the tab 11 with fingers, cotton forceps, hemostats, or similar instruments. The tab 11 may extend outwards a short distance or neatly cover and lay atop the non-free end. With this, removal of the film 3 may be achieved by simply peeling back and pulling the tab on the free end 11 of the film. The film 3 will take with it any excess cement which may have flowed out of the crown cavity 10 upon cementation.

As shown in FIG. 1-8, in general, the film 3 will lay flat covering the annular protuberances 9, however, the film's outer edge 3 may be bent directionally towards the crown 5, creating a J-shaped ridge 16. The J-shape ridge 16 will extend around the entire apical edge 7 and/or coronal edge, forming a shallow region that catches and prevents the flow of excess cement, before film 3 removal. Additionally, a bead or trough may be integrated into the film, around the aforementioned edge to assist with structural support and performance of the region that catches and holds excess cement.

As shown in FIG. 1-8, in the preferred embodiment of the present invention, the film 3 may be placed on the abutment 2 by the manufacturer prior to adjusting or prepping the abutment for the crown or simply by the dental lab or dentist him/herself.

Although the invention has been explained in relation to its preferred embodiment, it is to be understood that many other possible modifications and variations can be made without departing from the spirit of the scope of the invention.

The invention claimed is:
1. An dental implant device comprising:
   a fixture;
   an abutment telescopically insertable into and fixedly attachable to the fixture;
   a crown affixed to the abutment by a cement;
   a protective film positioned proximate the abutment for receiving the cement and for allowing removal for excess cement after affixation of the crown to the abutment; and
   the protective film covering, with a free end thereof overlapping on a top of a non-free end thereof, an entirety of an annular protuberance between the fixture and a margin of the crown.
2. The dental implant device of claim 1 wherein the annular protuberance is interposed between the abutment and the crown, the protective film is selectively affixable to the annular protuberance so as to receive the crown and the cement and to be selectively removable from the abutment after the cement has adhesively joined the crown to the abutment and the annular protuberance.
3. The dental implant device of claim 2 wherein the protective film a free end may be grasped by the user for removal of the protective film following adhesion of the crown to the annular protuberance.

4. The dental implant device of claim 2 wherein the protective film further includes a J-ridge formed at a first edge of the protective film and extending therefrom for positioning the protective film upwardly relative to the abutment so as to provide easy access for removal of the protective film as required.

5. The dental implant device of claim 4 in which the protective film includes a free end tab for facilitating removal of the protective film from the abutment as required so as to allow removal of excess cement after adhesion of the crown to the abutment.

6. The dental implant device of claim 1 wherein the protective film is selected from the group consisting of polytetrafluroethylene, cellulose film, polyvinyl chloride, polyvinylurethane, silicone and other natural and artificial polymers.

7. The dental implant device of claim 1 wherein the cement is selected from the group comprising consisting of zinc phosphate, glass ionomer, resin modified ionomer and a resin cement.

8. The dental implant device of claim 4 wherein the protective film extends out from below the patient's gum line and overlaps a second end of the protective film and is removable by means of fingers, cotton, forceps, hemostat, or a similar instrument so that when the protective film is pulled off of the annular protuberance it takes with it any cement which may have flowed out when the crown was sealed and cemented.

9. The dental implant device of claim 8 wherein the protective film may be shaped into annular shaped type ridge or bead at an apical end to catch and prevent excess cement from extending past the junction of the abutment and the implant body or at a coronal edge of the abutment as to prevent excess cement from extending past the junction of the crown and the abutment.

10. The dental implant device of claim 7 wherein the resin cement is selected from the group consisting of a light cured cement, a dual cured cement and an auto-cured cement.

11. The dental implant device of claim 2 wherein the protective film may be held in place electrostatically.

12. The dental implant device of claim 2 wherein the protective film may be modified to a shape in which it has an annular J-type ridge or bead at an apical edge to catch and prevent excess cement from extending past the junction of the abutment and the implant body or the coronal edge of the crown.

13. The dental implant device of claim 1 wherein the free end of the protective film extends from a soft tissue of a patient and is able to be grasped for removal and is able to be not broken or torn upon removal.

14. The dental implant device of claim 2 wherein the protective film is radiopaque to assure that there is no tape or film remaining on the abutment post-removal.

15. The dental implant device of claim 1 wherein the fixture comprises a shaft and a threaded cavity, and the abutment comprises an apical end and a non-apical end onto which the crown is affixed and the annular protuberance between the abutment and the crown.

16. The dental implant device of claim 1 wherein the abutment is a rigid member with an apical end that is coupled to the fixture via a screw or force fit that sits opposite a non-apical end of the abutment, the crown is cemented onto the non-apical end of the abutment which engages with and is received by a cavity of the crown cavity, the crown is secured to the abutment by the cement placed in the cavity of the crown on and by the non-apical end of the abutment.

17. The dental implant device of claim 1 wherein the annular protuberance is the widest portion of the abutment and sits parallel to and in between an apical end which is inserted into the fixture and a non-apical end which receives the crown, the annular protuberance's surface is positioned either sub-gingival or supra-gingival.

18. The dental implant device of claim 1 wherein a cavity of the crown is shaped and dimensioned to receive an entirety of a prepared portion of the abutment.

19. The dental implant device of claim 1 wherein the protective film comprises an adhesive on one or both sides thereof so as to prevent the protective film from coming off of the abutment or shifting and a tab which extends outwardly a distance from the annular protuberance and lays atop the non-free end of the protective film so that removal is achieved by peeling back and pulling the tab on the free end of the protective film.

20. The dental implant device of claim 1 wherein the protective film lays flat around the annular protuberance, and an outer edge of the protective film is bent directionally towards the crown, creating a J-shaped ridge, the J-shape ridge extends around an entire apical edge and/or a coronal edge of the abutment so as to form a shallow region that catches and prevents the flow of excess cement before film removal.

21. The dental implant device of claim 20 wherein the protective film includes a bead or trough which may be integrated into the protective film around the aforementioned edge to assist with structural support and performance of the portion of the protective film that catches and holds excess cement.

* * * * *